United States Patent
Mayer (10) Patent No.: US 10,057,505 B2
(45) Date of Patent: Aug. 21, 2018

(54) FULL-BODY IMAGE CAPTURING AND IMAGE PROCESSING SYSTEM AND METHOD FOR ITS OPERATION

(71) Applicant: FOTOFINDER SYSTEMS GMBH, Bad Birnbach (DE)

(72) Inventor: Andreas Mayer, Passau (DE)

(73) Assignee: FOTOFINDER SYSTEMS GMBH, Bad Birnbach (DE)

( * ) Notice: Subject to any disclaimer, the term of this patent is extended or adjusted under 35 U.S.C. 154(b) by 92 days.

(21) Appl. No.: 15/318,412

(22) PCT Filed: Apr. 16, 2015

(86) PCT No.: PCT/EP2015/058260
§ 371 (c)(1),
(2) Date: Dec. 13, 2016

(87) PCT Pub. No.: WO2015/188964
PCT Pub. Date: Dec. 17, 2015

(65) Prior Publication Data
US 2017/0150064 A1    May 25, 2017

(30) Foreign Application Priority Data

Jun. 13, 2014   (DE) .................. 10 2014 108 357

(51) Int. Cl.
*H04N 5/265* (2006.01)
*H04N 7/18* (2006.01)
(Continued)

(52) U.S. Cl.
CPC .......... *H04N 5/265* (2013.01); *A61B 5/1077* (2013.01); *A61B 5/445* (2013.01); *A61B 5/742* (2013.01);
(Continued)

(58) Field of Classification Search
CPC .......... H04N 5/265; H04N 7/183; G06T 7/11; G06T 7/0012; G06T 2207/30088; A61B 5/1077; A61B 5/445; A61B 5/742
See application file for complete search history.

(56) References Cited

U.S. PATENT DOCUMENTS

| | | |
|---|---|---|
| 2008/0049990 A1 | 2/2008 | Melchi et al. |
| 2009/0005693 A1* | 1/2009 | Brauner ................. A61B 5/413 600/481 |

(Continued)

FOREIGN PATENT DOCUMENTS

| | | |
|---|---|---|
| DE | 112011100032 T5 | 5/2013 |
| WO | WO2004095372 A1 | 11/2004 |

(Continued)

*Primary Examiner* — Hung Dang
*Assistant Examiner* — Sunghyoun Park
(74) *Attorney, Agent, or Firm* — King & Schickli, PLLC (57) ABSTRACT

A method for operating a full-body image capturing and image processing system, comprising at least the method steps of:
  capturing digital images of a body to be examined;
  creating at least one combined image from at least two different images;
  identifying skin surface of the body to be examined in the images and/or combined images;
  identifying predefined segments of the identified skin surface in the images and/or combined images;
  identifying skin regions that show reddening or scabbing in the images and/or combined images;
  calculating the proportional area of the identified skin region per segment;
  determining a degree of reddening of the skin surface, the degree of scabbing of the skin surface and a degree of curvature of the skin surface in the identified skin regions per segment;
  calculating one segment value each;
(Continued)

calculating a weighted total value;
outputting the total value and/or the segment values.

16 Claims, 3 Drawing Sheets

(51) Int. Cl.
    *G06T 7/11*     (2017.01)
    *G06T 7/00*     (2017.01)
    *A61B 5/00*     (2006.01)
    *A61B 5/107*     (2006.01)

(52) U.S. Cl.
    CPC .............. *G06T 7/0012* (2013.01); *G06T 7/11* (2017.01); *H04N 7/183* (2013.01); *G06T 2207/30088* (2013.01)

(56) References Cited

U.S. PATENT DOCUMENTS

| | | | |
|---|---|---|---|
| 2009/0281420 | A1 | 11/2009 | Passmore |
| 2010/0159497 | A1* | 6/2010 | Kimia ............... G06T 7/0012 435/29 |
| 2010/0272333 | A1 | 10/2010 | Stephan et al. |
| 2011/0103657 | A1* | 5/2011 | Kang ............... G06K 9/6215 382/128 |
| 2014/0043458 | A1* | 2/2014 | Cha ............... G06F 19/321 348/77 |
| 2016/0239956 | A1* | 8/2016 | Kang ............... G06T 17/005 |

FOREIGN PATENT DOCUMENTS

| | | |
|---|---|---|
| WO | WO2006078902 A2 | 7/2006 |
| WO | WO2007037848 A2 | 4/2007 |
| WO | WO2012064170 A1 | 5/2012 |

\* cited by examiner

FULL-BODY IMAGE CAPTURING AND IMAGE PROCESSING SYSTEM AND METHOD FOR ITS OPERATION

FIELD OF THE INVENTION

The invention relates to a full-body image capturing and image processing system and to a method for operating a system of this kind.

BACKGROUND OF THE INVENTION

Within the scope of treating psoriasis, it is known to create what is known as a Psoriasis Area and Severity Index (PASI) and to document the course of the disease and the course of treatment using said index. So far, PASI has been determined manually or as a rough calculation or in the course of an estimate following examination of the skin surface of a patient. However, this determination has the disadvantage that it can only be carried out by highly specialized, medically trained and experienced professionals. Furthermore, determining PASI is highly time-consuming due to the time required for examining the entire skin surface. Finally, the most serious disadvantage in the previous determination of PASI is the fact that while there are basic criteria and an attempt to standardize PASI, they are applied differently by each user and even from patient to patient or even from examination to examination. As a consequence, the comparability of the determined values, the reproducibility of the determined values and, correspondingly, the entire informative value of the determined values of PASI in general decrease significantly.

SUMMARY OF THE INVENTION

Hence, the object of the present invention is to provide a system and a method for operating such a system that automates the determination of PASI to the furthest extent and thus drastically reduces the time required and, at the same time, highly objectifies the creation of PASI and thus significantly improves its informative value and its reproducibility.

This object is attained by a method according to claim 1 of the invention and by a device according to claim 12 of the invention. Advantageous embodiments of the method and of the device are the subject-matter of the dependent claims.

The method according to the invention is used to operate a full-body image capturing and image processing system, which has at least an imaging system, a memory and a computing means comprising an image processing device, an evaluating means and output and input units of the system.

The method according to the invention envisages the following method steps:

First, digital images of a body to be examined are captured by the imaging system using a plurality of predetermined positions of the body to be examined in relation to the imaging system.

In another method step, at least one combined image is created by means of the image processing device from at least two different images of the same position of the body to be examined. It may be envisaged for the images of the body to be examined created by the imaging system to be transmitted to the memory for storage and for the computing means, in particular the image processing device, to be able to utilize the content of the memory, i.e. to access the images created with the imaging system and to correspondingly process them.

In another step of the method, the skin surface of the body to be examined is identified in the images and/or combined images by means of the image processing device. For this purpose, it may be envisaged, for example, that a captured image and/or combined image is converted to the YCbCr color model, subsequently the Cr component, i.e. the red-green-crominence portion of the image or combined image, is filtered out and subsequently the skin surface is identified using an ETP algorithm. This means that, as a result, pixels that represent the skin surface of the body to be examined in the images or combined images are identified in the images or combined images by their respective position or address.

In another method step, it is envisaged that segments predefined in advance are identified for the skin surfaces identified in the images or combined images. In other words, this means that different parts of identified skin surface in different images or combined images are summarized because they show an identical anatomical segment of the body to be examined from different perspectives or from different positions of the body to be examined in relation to the imaging system. So it is envisaged for the entire identified skin surface in images or in the combined images to be attributed to one segment each. This means that pixels from different images or combined images are attributed to one and the same segment. In this way, calculation of PASI as a whole is based on anatomical segments instead of on the individual images or combined images. The image processing device can perform the method step of segmentation using commonly known shape-recognition algorithms.

In another method step, skin regions of the identified skin surface that show reddening or scabbing, i.e. plaque formation, are identified in the images or combined images. This means that the lesions on the skin surface are identified in total, the properties reddening and scabbing being used for identification. Identification again takes place by means of the image processing device to determine or identify skin regions in the images or combined images that show plaque or scab. The images can be filtered or processed in such a manner that colorless or white areas of the images are highlighted or filtered out. This may take place in such a manner that the images are converted to the HSV image standard and only the S and V channels of the image or images are subsequently taken into account. As stated above, owing to the earlier segmentation of the images or combined images, identification in the individual images or combined images simultaneously leads to identification with respect to the individual segments.

In another method step, the proportional surface of the identified skin region per segment is calculated by means of the evaluating means. For this purpose, the skin regions of the identified skin surface that are identified as reddened or scabbed and which are attributed to a specific segment are each summarized from different images or combined images and both the total skin surface and the surface of the identified skin region are determined and put in relation to each other. Calculation is performed by means of the evaluating means of the computing means.

In another method step, the degree of reddening of the skin surface, the degree of scabbing or plaque formation on the skin surface and the degree of curvature of the skin surface in the identified skin regions is determined for each segment by means of the image processing device. For this purpose, again, image processing methods known per se are employed. To determine the degree of reddening, for example, the image or the combined image is converted to the LAB color mode and the image or the combined image is filtered in such a manner that strongly red pixels are depicted very brightly and pixels less red are correspondingly depicted less brightly. Subsequently, the brightness distribution can additionally be filtered by means of a Gaussian filter, for example. In this way, a more even distribution can be achieved. To calculate the curvature or the degree of curvature, the images or combined images can be converted to grayscale images and can be correspondingly filtered with a first order Sobel filter. This leads to the occurrence of bright areas in areas of strong curvature. The degree of scabbing or plaque formation can be calculated by multiplying the relative proportion of the identified skin regions on which plaque or scab has been identified by a constant factor. All in all, as a result of this method step, numerical values are obtained for the degree of reddening, the degree of scabbing and the degree of curvature that may be integers between 0 and 4, for example.

In another method step, one segment value each is calculated based on the degree of reddening of the skin surface, the degree of scabbing or plaque formation on the skin surface, the degree of curvature of the skin surface and the proportion of identified skin regions on the skin surface per segment by means of the evaluating means. The respective segment values are scaled in such a manner that a minimum segment value of 0 (zero) and a maximum segment value of 6 is reached per segment.

The method step can be designed in such a manner that the each of the degrees of reddening, scabbing and curvature determined are added. Furthermore, multiplication of the resulting value with an integer value may be envisaged, said integer value representing the proportional area of the identified skin region per segment. For instance, it may be envisaged that the value between 0 and 6 is assigned according to the following table of proportional area of the identified skin region:

| 0: | 0% |
| 1: | 1-9% |
| 2: | 10-29% |
| 3: | 30-49% |
| 4: | 50-69% |
| 5: | 70-89% |
| 6: | 90-100% |

The percentages correspond to the proportional area of the identified skin region.

In an additional method step, a weighted total value is calculated based on the segment values and one weighting factor for each segment value. This calculation, too, is performed by the evaluating means of the computing means. It may be envisaged, for example, that the weighting factors vary between 0.1 and 0.4. The weighting factor may correspond to the average proportion of the skin surface of the respective segment in the entire skin surface of an average body to be examined, for example. In this case, it is envisaged for the sum of the weighting factors per se to have a value of 1 in total. Furthermore, it may be envisaged that the total value is the sum of the weighted segment values.

In a concluding method step, the total value and/or the segment values is/are outputted by means of an output unit.

With the proposed method, it becomes possible to automate the creation of a PASI or of a weighted total value from the recording of the body to be examined, i.e. from the capturing of the digital images, to the ultimate calculation and outputting of the PASI or of the total value or of the segment values to the furthest extent and to additionally make it highly reproducible.

One the one hand, this enables laypersons or personnel with little training to perform and/or monitor such activities, i.e. the creation of the PASI or of the total value. Furthermore, the already available and ever-increasing computing power of known computing means allows the entire method to be carried out in an extremely short time once the images have been captured. As a matter of fact, it is even possible to begin working on other intended method steps while the images are still being captured, which means further shortening of the time required for performing the method. Finally, by moving the identifying and calculating method steps to a computing means, a very high reproducibility of the results can be achieved.

According to an embodiment of the method according to the invention, combined images are created identifying identical areas in at least two images and merging the images subsequent to the identification of identical areas in such a manner that the identified areas show an overlap of the original images in the identified areas. In other words, this means that duplicates or areas of the body to be examined that are depicted twice or multiple times are removed in the course of the creation of the combined images. In this way, it is ensured that, on the one hand, the entire body to be examined has been depicted, but that the body to be examined has not been depicted twice, which would lead to a distortion of the total value or of the segment values. In addition, the combined images are of particular advantage if the predefined segments are designed in such a manner that they would span across several individual images even if the position of the body to be examined stayed the same relative to the imaging system. In such a case, the segments would have to be divided and identified in a correspondingly divided manner. However, this leads to a faultier or less certain recognition of the segments.

In addition, it is particularly desirable for the images and/or the combined images to be outputted on the output unit in the course of the method. This may be appropriate and advantageous, as will become clearer hereinafter, at different points or at different stages of progression of the entire method. However, it can be advantageous in principle for the images and/or combined images to be outputted on the output unit after capturing and/or creation.

If the images and/or combined images are outputted on the output unit, it can be especially advantageous if the skin regions or lesions identified therein are also displayed in the images and/or in the combined images. To this end, it may be envisaged, for example, that colored shadings or colored semitransparent areas which match the identified skin regions are displayed in the images or combined images.

Furthermore, it is particularly desirable if the identified skin regions can be changed and/or removed and/or additional identified skin regions can be defined by an input at the input unit. In this way, a correction can be made, for example, in case the automatic identification of skin regions as performed by the image processing device is incomplete or incorrect due to lighting conditions or the like. In such a case, when the images are displayed on the output unit, an operator of the system or a user of the method can quickly and easily spot, in a display of the identified skin regions, the regions in the images in which the identification was incorrect, incomplete or has not happened at all and can correspondingly make the correction by means of an input via the input unit. In this way, it becomes possible to overcome the limitations of automatic image processing and to still avail oneself of the speed of automatic image processing.

Moreover, it may be especially advantageous for the segments, too, to be displayed on the output unit. This may entail a schematized output of predefined images or combined images in which the segments are displayed. Alternatively, however, the segments can also be displayed in the images or combined images. For this purpose, too, it may be envisaged for the corresponding pixels of the images or combined images to be optically highlighted, in particular by color.

In the case mentioned last in which the identified areas attributed to a segment are also displayed in the images and/or combined images displayed on an output unit, it is further particularly advantageous if the segments can be changed by an input via the input unit. This correction, too, can combine in a particularly advantageous fashion the speed of an automatic identification of the segments in the images or combined images and a later manual and potentially more precise correction.

Furthermore, it is particularly desirable for the areas head, upper extremities, legs and torso to be identified as segments in the identified skin surface of the images or combined images. In this way, a segmentation is achieved that is also used for manual creation and calculation of PASI.

To furthermore prevent a false interpretation by the image processing device and/or the evaluating device, it can be advantageous if the segment values and/or the weighted total value can be changed by an input of the input unit.

Furthermore, it may be envisaged that the transition between different method steps of the method according to the invention is triggered in response to an input of the input unit. While this does slightly diminish the total speed towards obtaining the weighted total value or toward obtaining PASI, it becomes possible at the same time to monitor the individual method steps and, if need be, to act on the individual method steps in a correcting or at least verifying manner by means of an input, as described above.

In order to add further special advantages to the method beyond a single process regarding a body to be examined, it is particularly desirable for the calculated weighted total value to be stored in the memory. In this way, it is possible to document and compare the progress of a therapy and the development of the symptoms. Aside from the weighted total value being stored, it may also be advantageously provided for the segment values, the calculated proportional area of the identified skin regions per segment, the identified skin regions, the identified predefined segments and the identified skin surface of the body to be examined to be stored in the memory at least indirectly after their identification. In this way, in addition to a comparison of the results, i.e. of the segment values or of the weighted total value, a change regarding the characteristics mentioned above can be determined in the course of a repeated application of the method to the same body to be examined.

The object according to the invention is also attained by a fill-body image capturing and image processing system which comprises an imaging system for capturing digital images of a body to be examined using a plurality of predefined positions of the body to be examined, the imaging system having at least a capturing means and an automatic adjusting means. Furthermore, a memory connected to the imaging system and at least configured to store digital images and a computing means comprising an image processing device and an evaluating means are provided, the computing means being connected to the memory and additionally comprising an output unit and an input of the full-body image capturing and image processing system.

The inventive nature of the system is achieved in that the image processing means is configured to create combined images from at least two different images of the same position of the body to be examined, to identify skin surface of the body to be examined in the images or combined images, to identify predefined segments of the identified skin surface in the images or combined images, to identify skin regions in the images and/or combined images that show reddening or scabbing or plaque formation, and to determine a degree of reddening of the skin surface, a degree of scabbing of the skin surface or a degree of curvature of the skin surface in the identified skin regions for each segment, and in that the computing means is configured to calculate a proportion of identified skin regions in the identified skin surface per segment, to calculate segment values based on the degree of reddening of the skin surface, the degree of scabbing of the skin surface, the degree of curvature of the skin surface and the proportion of the skin surface in identified skin regions and to calculate a weighted total value based on the segment values and on one weighting factor for each segment value.

The full-body image capturing and image processing system allows quick, reliable and reproducible determination of the weighted total value in the form of a PASI without any participation of highly specialized operators or users. Moreover, the design of the system allows monitoring and comparing of the progression of a therapy and of a disease.

According to an advantageous embodiment, the memory is also configured to store data regarding the body to be examined, combined images, segment values and weighted total values. In this way, on the one hand, automatic control of the imaging system and thus automatic capturing of digital images of a body to be examined can be achieved. In addition, storing combined images, segment values and weighted total values allows a comparison with previous results of the use of the system for the identical body to be examined. In addition, it may also be provided for the memory to be configured to store the data regarding the images or combined images created by means of the image processing device. Among other things, the identified skin regions, the identified proportion of the skin regions in the entire skin surface or other data obtained from the images by means of the image processing device can be stored, for example. This, too, allows improved analysis of the progression of the disease and of the treatment of the disease over time.

It is also advantageous that the full-body image capturing and image processing system is designed in such a manner that the adjusting means is controlled by a controller and controls the capturing means as a function of data regarding the body to be examined and of the position of the body to be examined. For example, it may be envisaged that data regarding the body to be examined, such as size and gender, are inputted via the input unit and are stored in the memory. The controller can be configured in such a manner that it can access said data regarding the body to be examined and can generate corresponding control signals for controlling the capturing means. In this way, on the one hand, precise and quick capturing of the digital images of the body to be examined is made possible. Moreover, this also allows achieving reproducible capturing of images as the system is repeatedly used.

Furthermore, it is advantageous if the output unit is realized as a screen and/or as a printer. It is particularly advantageous if the system comprises both a screen and a printer. By means of the screen, user interaction may take place, for example, and by means of the printer, results generated with the system can be recorded and documented, for example.

Hereinafter, exemplary embodiments of the present invention will be explained by way of example with the aid of merely schematic drawings.

DETAILED DESCRIPTION OF THE INVENTION

Figure 1:
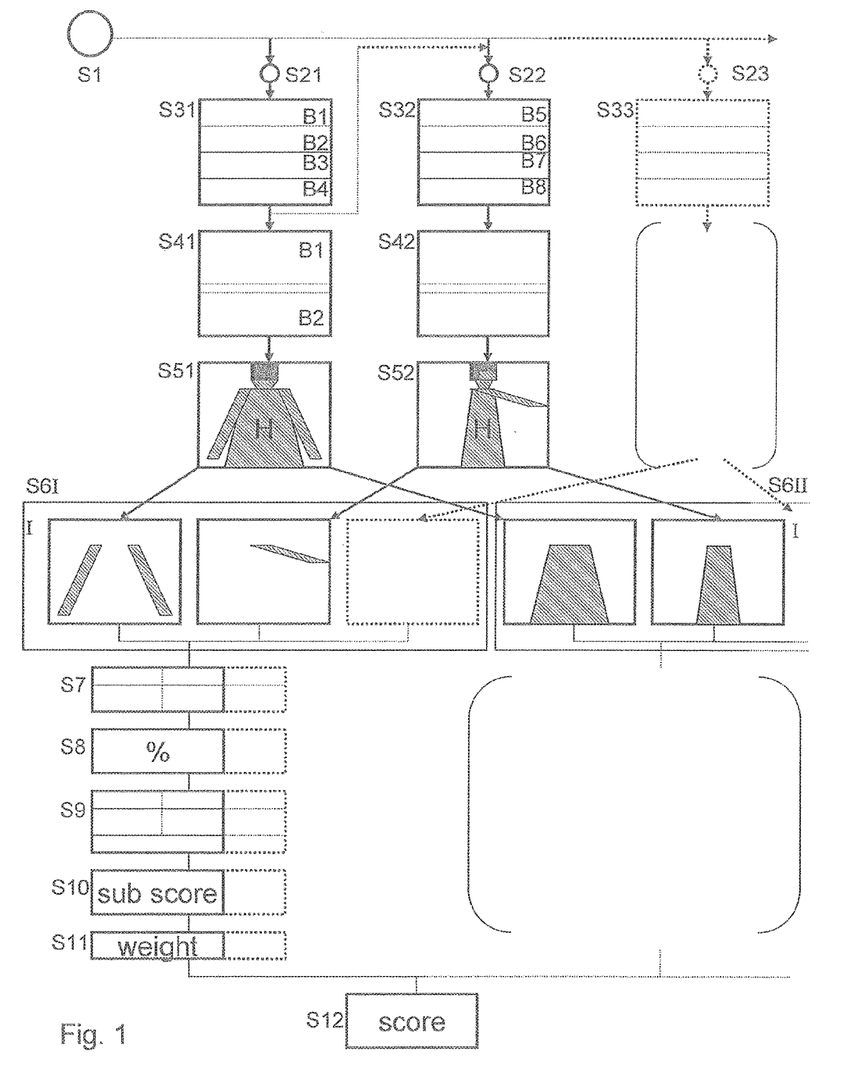
FIG. 1 shows a schematized flow chart of a part of the method according to the invention.

FIG. 1 shows a section of the method according to the invention, which begins with method step S1 and ends with method step S12. In method step S1, a set of data or data regarding the body to be examined is inputted via an input unit or a corresponding set of data is selected from the memory by means of the input unit.

In steps S21, S22 and S23 and in the other method steps, which are not illustrated in FIG. 1, a controller of the imaging system generates control commands therefrom for controlling the adjusting means of the imaging system, by means of which the capturing means is controlled. The signals generated in steps S21, S22 and S23 each relate to a different position of the body to be examined in relation to the imaging system.

In method steps S31 to S33 and in the other method steps envisaged but not illustrated in FIG. 1, the images are captured by means of the imaging system. For example, images B1 to B4 are created in step S31 in a first position of the body to be examined. Accordingly, images B5 to B8 are created in step S32.

In method steps S41 and S42, combined images are created from all images captured in step S31 or from at least two images captured in step S31 if doing so is envisaged for the respective position of the body to be examined. It may be envisaged, for example, that step S41 and step S22 are initiated simultaneously, which is indicated by the dashed-line connection in FIG. 1. In other words, this means that while the image processing device is combining the images of step S31 at least partially into combined images, new control signals can already be generated and executed to capture the images B5 to B8, which are to be captured in step S32. The same also applies to the parallel implementation of other method steps. The flows illustrated in FIG. 1 relate to one possible sequence of the individual steps. Yet, a deviating sequence is possible, as well, as long as the order stays unchanged in such a way that the intermediate results or pre-processing steps required in each method step are generated prior to the respective method step.

Hence, step S42 also corresponds to a generation of combined images from the images of step S32. In steps S51 and S52, which are potentially carried out in a delayed manner, skin surface H is depicted in the images or combined images is extracted or identified from the captured images or generated combined images by means of the image processing device. As indicated in steps S51 and S52, the exemplary combined images show a rear view and a side view, respectively, of the body to be examined.

Accordingly, another position of the body to be examined can be processed in the branch of the method initiated by method step S23. The same applies to other method steps which are not illustrated.

In steps S6I and S6II, the surface attributed to each segment is correspondingly extracted from the previously identified skin surfaces. For example, in method step S6I, the pixels of the images or combined images that show or represent the segment of the upper extremities are extracted or identified. In method step S6II, correspondingly, the skin surface or the corresponding pixels of the respective images or combined images that are attributed to the torso segment are extracted and summarized.

The other method steps S7 to S12 are described merely for the segment of the upper extremities summarized in method step S6I. Method steps S7 to S12 are analogously applied to the remaining segments, as identified by way of example in method step S6II.

In method step S7, skin regions that show reddening or scabbing or plaque formation are identified in the identified skin surfaces attributed to the segment.

In subsequent method step S8, the proportion of the skin region determined in step S7 in the entire skin surface attributed to the segment is determined. This entails a conversion into an integer numerical value between 0 and 6 according to the table above.

In step S9, using corresponding algorithms, the degree of reddening of the skin surface, the degree of scabbing of the skin surface and the degree of curvature of the skin surface in the identified skin regions is calculated. The calculation comprises a scaling to an integer numerical value between 0 and 4.

In subsequent method step S10, a segment value (sub-score) is calculated from the results of method steps S8 and S9. Subsequently, the segment value is weighted with a weighting factor in method step S11. From the segment value obtained in step S11 as in comparable steps of other segments, the total value or the weighted total value is calculated in final method step S12 and is outputted on an output unit.

In conclusion, the purely mathematical determination of the PASI total value or score, which is based on the corresponding image processing steps, can be summarized as follows:

$$\text{Score} = \sum_{i=1}^{n} g_i \cdot r_i \cdot (GR_i + GS_i + GW_i),$$

$i=i^{th}$ segment;
n=number of segments=4;
$GR_i$=degree of reddening, $\{0, 1, \ldots, 4\}$;
$GS_i$=degree of scabbing, $\{0, 1, \ldots, 4\}$;
$GW_i$=degree of curvature, $\{0, 1, \ldots, 4\}$
r=proportional area of the identified skin surface, $\{0, 1, \ldots, 6\}$;
$g_i$=weighting factor, $\{0.1; 0.2; 0.3; 0.4\}$.

In the case of a calculation with four segments, segments for the head and neck area, the upper extremities, the torso and the lower extremities may be envisaged, for example. In this case, it may be envisaged that a weighting factor of $g_1=0.1$ is attributed to the segment of the head and neck area, a weighting factor of $g_2=0.2$ is attributed to the segment of the upper extremities, a weighting factor of $g_3=0.3$ is attributed to the segment of the torso and a weighting factor of $g_4=0.4$ is attributed to the segment of the lower extremities. This results in a total sum of the weighting factors of 1 even.

Figure 2:
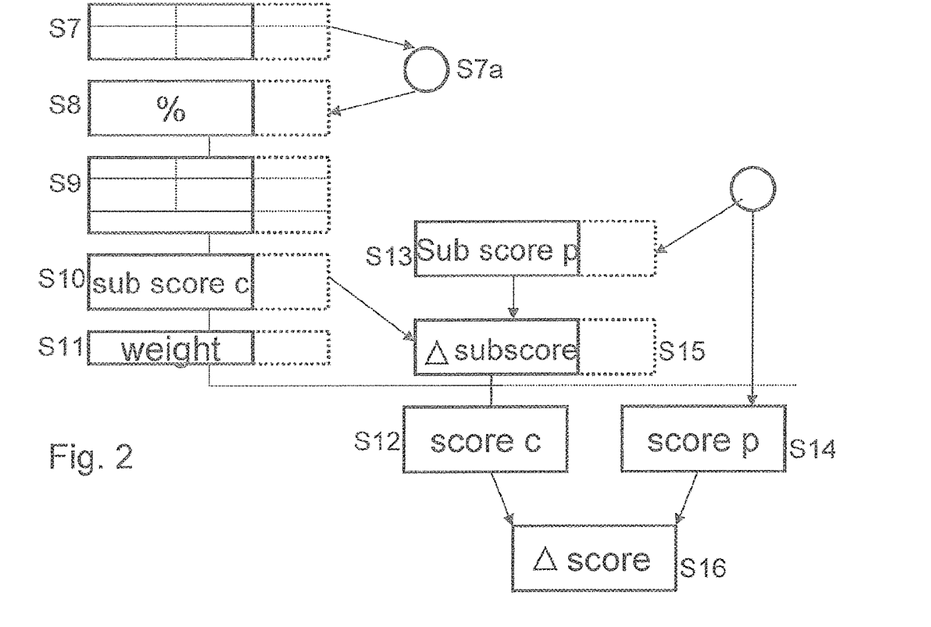
FIG. 2 shows a schematized flow illustration of a part of the method according to the invention according to a variation.

FIG. 2 shows a variation of the method according to the invention. In FIG. 2, it is envisaged that subsequent to method step S7, i.e. subsequent to the identification of the skin regions that show reddening or scabbing, an input is made by means of the input unit in Step S7a. It may be envisaged, on the one hand, that the input in step S7a merely serves to transition between step S7 and step S8, i.e. to initiate step S8. On the other hand, it may also be envisaged that the results of step S7 are corrected by means of the input at the input unit before step S8 is initiated.

Furthermore, the variation in FIG. 2 is an implementation of the method for a body to be examined for which the method has already been performed in the past, the results or intermediate results of the method having been stored in the memory of the system. Accordingly, in method steps S13 and S14, a segment value and a weighted total value are retrieved from the memory and are compared to the segment value calculated in step S10 and with the total value calculated in step S12, respectively. In this way, in steps S15 and S16, the change of the segment value and the change of the weighted total value are calculated, respectively, and may be outputted on the output unit of the system.

Figure 3:
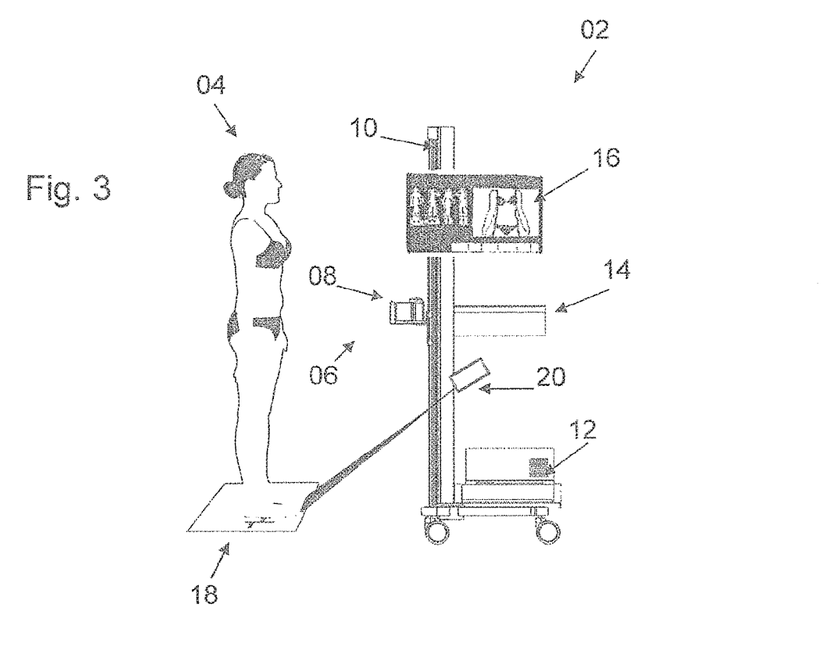
FIG. 3 shows a schematized illustration of the system according to the invention.

FIG. 3 shows a full-body image capturing and image processing system 02 according to the invention and a body to be examined 04. The body to be examined 04 is mapped in the form of digital images by means of an imaging system 08, the imaging system 08 having a capturing means 06 and an adjusting means 10. The height of the capturing means 06 can be adjusted by means of the adjusting means 10. The adjusting means 10 can be controlled by a controller (not illustrated), which can also control the triggering of the capturing means. The data regarding the body to be examined that are necessary to control the adjusting means can be stored in a memory, for example, which is arranged in the computing means 12. Alternatively, the data regarding the body to be examined can also be inputted by means of an input unit 14.

The system according to the invention further has an output unit 16 in the form of a screen. As for positioning the body to be examined relative to the imaging system, FIG. 3 shows a possible setup in which the body to be examined is positioned on a foot mat 18, the foot mat 18 having corresponding graphical illustrations, such as in the form of pictograms, which convey the respective position of the body to be examined.

To determine the distance between the body to be examined and the imaging system, a measuring means 20 can be additionally provided, which determines the distance between the full-body image capturing and image processing system and the foot mat 18, and thus indirectly the distance to the body to be examined, by means of suitable methods, such as optical measuring methods.

In the computing means 12, the device according to the invention has an image processing device and an evaluating means, which is configured to carry out the method according to the invention in connection with the memory and the imaging system.

Figure 4:
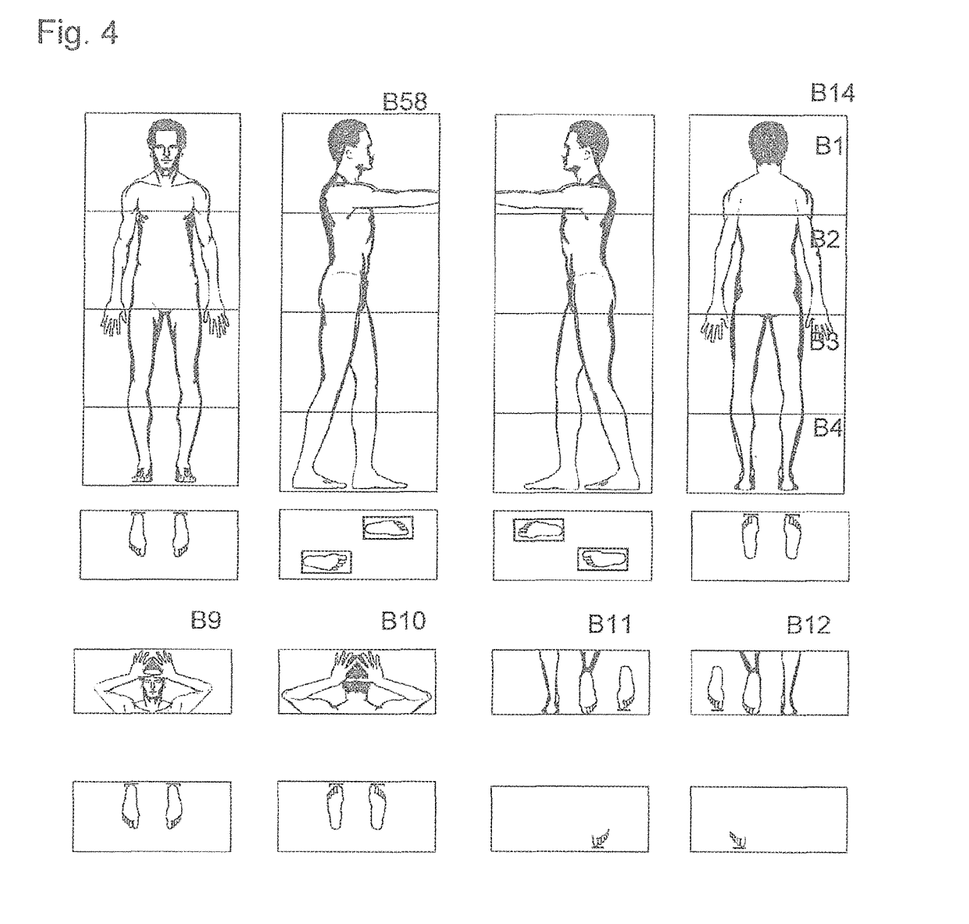
FIG. 4 shows a schematized illustration of images, combined images and corresponding positioning aids for positioning the body to be examined.

FIG. 4 shows a total of four combined images and four images that result from the digital capturings of the imaging system or are generated by means of the same. In addition, FIG. 4 shows the pictograms provided on the foot mat 18 in the respective combined images or images, which serve to help the body to be examined take the respective position in relation to the imaging system. FIG. 4 further shows the combined image from images B1 to B4, which was already illustrated in FIG. 1 by way of example. Also, FIG. 4 shows the combined image B58 from images B5 to B8, which was also schematically illustrated before in FIG. 1. The individual images B9 to B12, as captured by the imaging system for carrying out the method according to the invention, are also illustrated in FIG. 4.

The invention claimed is:

1. A method for operating a full-body image capturing and image processing system having an automatic imaging system, a memory and a computer comprising an image processor, a calculator and an output unit and an input unit, comprising at least the method steps of: capturing digital images of a body to be examined by means of the imaging system using a plurality of predetermined positions of the body to be examined; creating at least one combined image from at least two different images of the same position of the body to be examined by means of the image processor; identifying skin surface of the body to be examined in the images and/or combined images by means of the image processor; identifying predefined segments of the identified skin surface in the images and/or combined images by means of the image processor; identifying skin regions that show reddening or scabbing in the images and/or combined images by means of the image processor; calculating the proportional area of the identified skin region per segment by means of the calculator; determining a degree of reddening of the skin surface, the degree of scabbing of the skin surface and a degree of curvature of the skin surface in the identified skin regions per segment by means of the image processor; calculating one segment value based on each of the degree of reddening of the skin surface, the degree of scabbing of the skin surface, the degree of curvature of the skin surface and the proportion of the identified skin regions of the skin surface per segment by means of the calculator; calculating a weighted total value based on the segment values and one weighting factor for each segment value by means of the calculator; outputting the total value and/or the segment values by means of an output unit.

2. The method according to claim 1,
characterized in that
creating combined images comprises identifying identical areas in at least two images and merging the images with an overlap in the identified areas.

3. The method according to claim 1,
characterized in that the
images and/or the combined images are outputted on the output unit.

4. The method according to claim 3,
characterized in that
the identified skin regions are displayed in the images and/or combined images.

5. The method according to claim 4,
characterized in that the identified skin regions can be changed and/or removed and/or additional identified skin regions can be defined by an input at the input unit.

6. The method according to claim 3,
characterized in that
the segments are displayed in particular in the images and/or combined images.

7. The method according to claim 6,
characterized in that the segments can be changed by an input of the input unit.

8. The method according to claim 1,
characterized in that
the areas head, upper extremities, legs and torso are identified in the images and/or combined images as segments in the identified skin surface.

9. The method according to claim 1,
characterized in that the segment values and/or the weighted total value can be changed by an input of the input unit.

10. The method according to claim 1,
characterized in that
the transition between different method steps happens in response to an input of the input unit.

11. The method according to claim 1,
characterized in that the weighted total value is stored in the memory.

12. A full-body image capturing and image processing system having an imaging system for capturing digital images of a body to be examined using a plurality of predetermined positions of the body to be examined, the imaging system having an imager and an actuator, a memory connected to the imaging system and at least configured to store digital images, and a computer comprising an image processor and a calculator, an output unit and an input unit, the computer being connected to the memory, characterized in that the image processor is configured to create combined images from at least two different images of the same position of the body to be examined, to identify skin surface of the body to be examined in the images and/or combined images, to identify predefined segments of the identified skin surface in the images and/or combined images, to identify skin regions that show reddening or scabbing in the images and/or combined images, and to determine a degree of reddening of the skin surface, a degree of scabbing of the skin surface and a degree of curvature of the skin surface in the identified skin regions per segment, and the calculator is configured to calculate the proportional area of the identified skin regions per segment, to calculate one segment value based on each of the degree of reddening of the skin surface, the degree of scabbing of the skin surface, the degree of curvature of the skin surface and the proportion of the skin surface of the identified skin regions and to calculate a weighted total value based on the segment values and one weighting factor for each segment value.

13. The full-body image capturing and image processing system according to claim 12, characterized in that
the memory is configured to store data regarding the body to be examined, combined images, segment values and weighted total values.

14. The full-body image capturing and image processing system according to claim 13,
characterized in that the actuator is controlled via a controller, which controls the imager as a function of data regarding the body to be examined and of the position of the body to be examined.

15. The full-body image capturing and image processing system according to claim 12,
characterized in that the output unit is realized as a screen and/or as a printer.

16. A full-body image capturing and image processing system having an imaging system for capturing digital images of a body to be examined using a plurality of predetermined positions of the body to be examined, the imaging system comprising:
a computer including a memory configured to store digital images and an image processor configured to create combined images from at least two different images of the same position of the body to be examined, to identify skin surface of the body to be examined in the images and/or combined images, to identify predefined segments of the identified skin surface in the images and/or combined images, to identify skin regions that show reddening or scabbing in the images and/or combined images, and to determine a degree of reddening of the skin surface, a degree of scabbing of the skin surface and a degree of curvature of the skin surface in the identified skin regions per segment, the computer configured to calculate the proportional area of the identified skin regions per segment, to calculate one segment value based on each of the degree of reddening of the skin surface, the degree of scabbing of the skin surface, the degree of curvature of the skin surface and the proportion of the skin surface of the identified skin regions and to calculate a weighted total value based on the segment values and one weighting factor for each segment value.

* * * * *